United States Patent

Todori et al.

Patent Number: 5,937,267
Date of Patent: Aug. 10, 1999

[54] SYSTEM, DEVICE AND METHOD FOR QUANTIFICATION OF POLYCHLOROBIPHENYLS

[75] Inventors: Kenji Todori; Shuji Hayase, both of Yokohama; Katsushi Nishizawa, Ota-ku; Nobutada Aoki, Chigasaki; Hideki Shimada, Kawasaki; Naoki Tajima, Zushi; Kazuo Unoki, Yokohama, all of Japan

[73] Assignee: Kabushiki Kasiha Toshiba, Kawasaki, Japan

[21] Appl. No.: 08/886,542

[22] Filed: Jul. 1, 1997

[30] Foreign Application Priority Data

Jul. 2, 1996 [JP] Japan ................................. 8-172439

[51] Int. Cl.$^6$ ...................................................... B01J 19/12
[52] U.S. Cl. .......................................................... 422/186.3
[58] Field of Search ........................................... 422/186.3

[56] References Cited

FOREIGN PATENT DOCUMENTS 6-262171 9/1994 Japan .
6-304407 11/1994 Japan .
WO 93/13404 7/1993 WIPO .

Primary Examiner—Timothy McMahon
Attorney, Agent, or Firm—Oblon, Spivak, McClelland, Maier & Neustadt, P.C.

[57] ABSTRACT

The present invention is to clear the difficulty in determining the progress of the decomposition reaction of PCBs carried out by a conventional device for decomposing PCBs, and to provide a system for treating PCBs to render them harmless, capable of continuously determining the progress of the decomposition reaction of PCBs at real time by using a predetermined amount of a reaction solution taken out while the decomposition reaction of the PCBs is proceeding.

The quantity of the polychlorobiphenyls existing in a polychlorobiphenyl-containing liquid can be determined by the system for treating polychlorobiphenyls to render them harmless according to the present invention in the following manner: a polychlorobiphenyl-containing liquid is irradiated with exciting light of from 400 nm to shorter than 450 nm, that can excite the polychlorobiphenyls, or with exciting light of from 300 nm to shorter than 400 nm, that can excite the decomposition products of the polychlorobiphenyls, and the intensity of the emitted light is measured at a wavelength between 450 nm and 600 nm, both inclusive; and the quantity of the existing polychlorobiphenyls is determined based on one of the values measured, or based on the ratio between the two values measured. The progress of the decomposition reaction of the polychlorobiphenyls can thus be determined, and the polychlorobiphenyls can be fully and sufficiently decomposed.

15 Claims, 5 Drawing Sheets

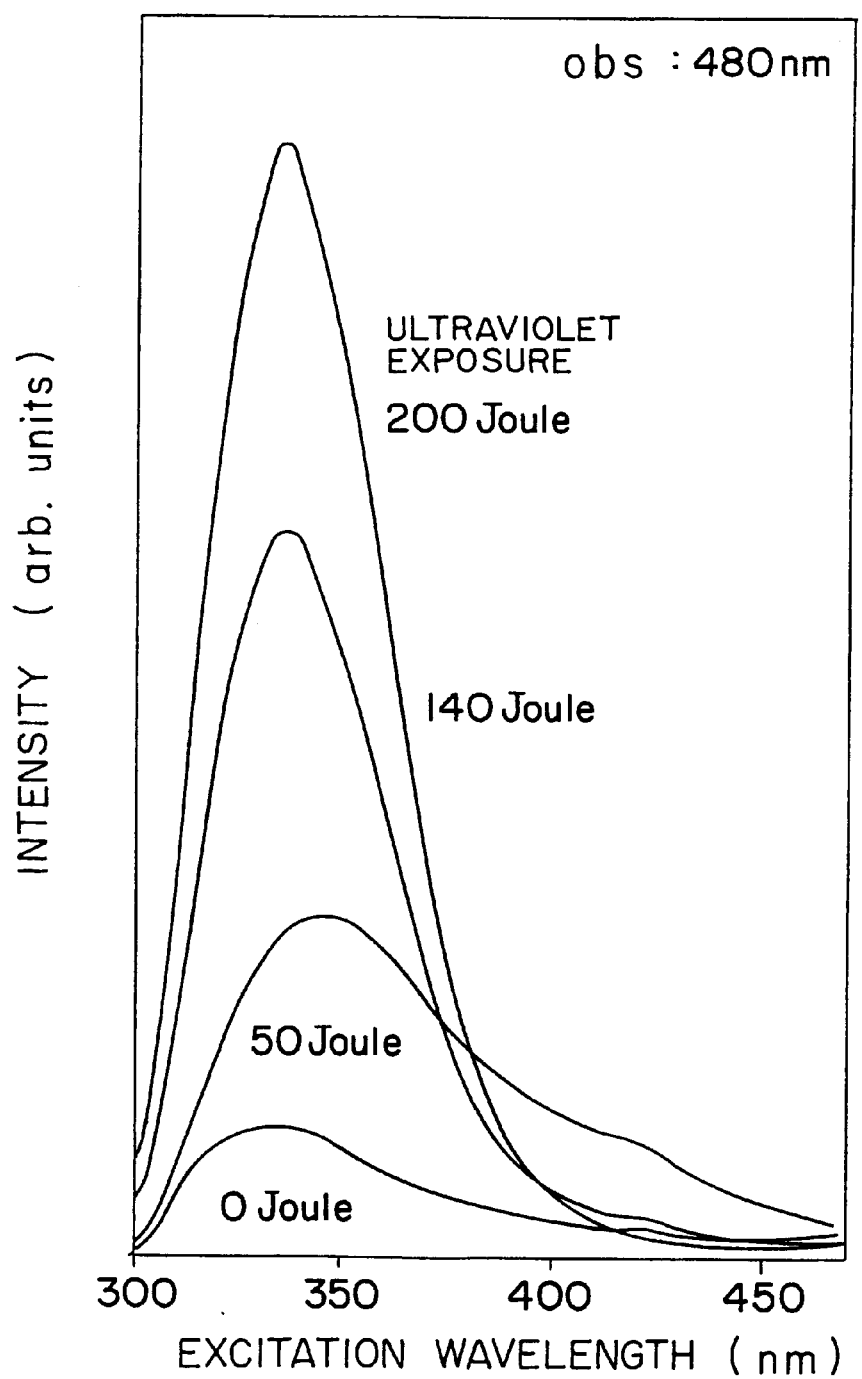
F I G. 1

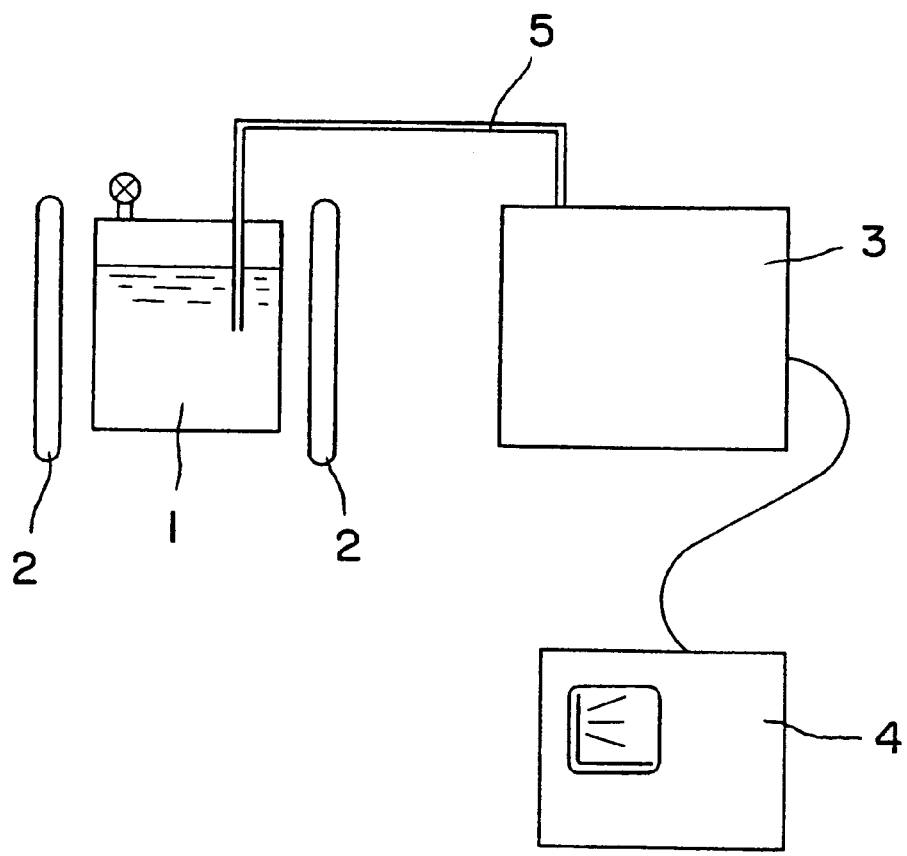
F I G. 2

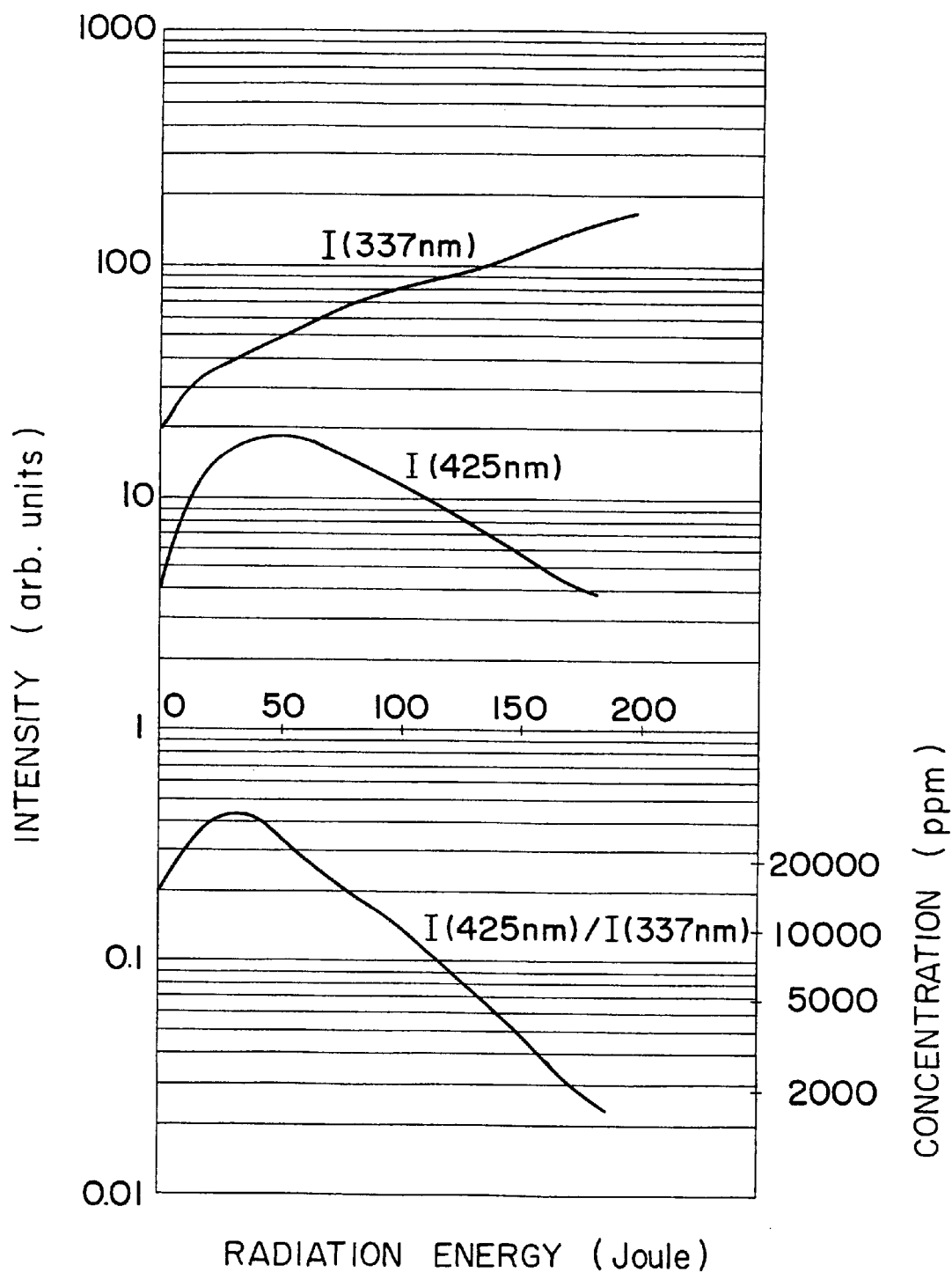
F I G. 3

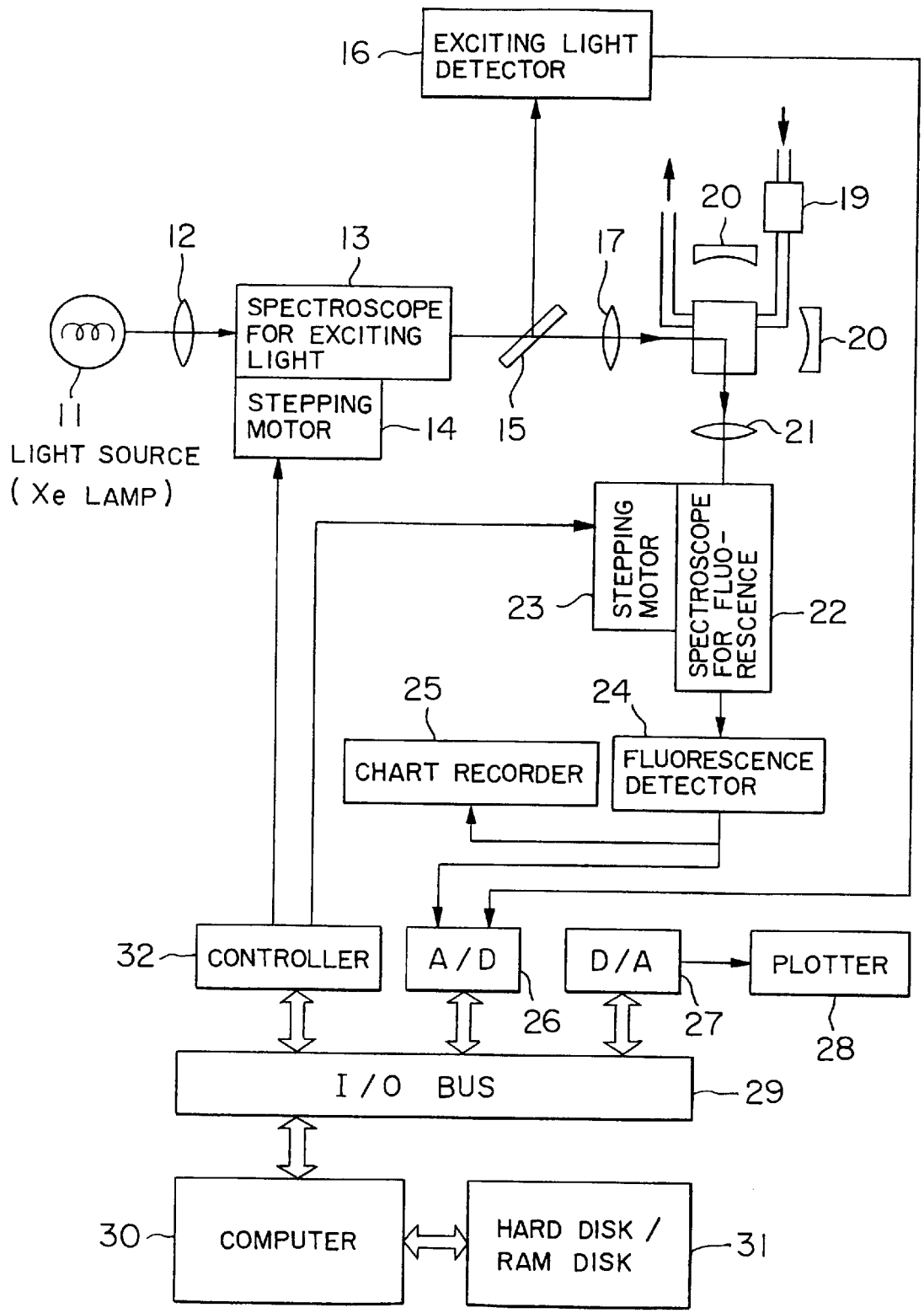
F I G. 4

SYSTEM, DEVICE AND METHOD FOR QUANTIFICATION OF POLYCHLOROBIPHENYLS

BACKGROUND OF THE INVENTION

1. Field of the Invention

The present invention relates to a system for treating polychlorobiphenyls to render them harmless by decomposing them.

2. Background of the Invention

Heretofore, polychlorobiphenyls (hereinafter abbreviated to "PCBs") have been widely used in the field of chemical industry. Since PCBs are characterized by having low heat capacity and good insulation properties, they have been used as insulating oils for condensers, transformers, etc., and for heat transfer media and the like. In recent years, however, it was found that PCBs are not only injurious to the human body but also bioconcentrated when absorbed in the human body. For this reason, the production and use of PCBs were prohibited by law in 1972 in Japan, and incineration at high temperatures was established as only one safety method for the disposal of PCBs. However, when PCBs are disposed under inadequate conditions, there is such a possibility that virulently poisonous dioxin is generated. It is therefore difficult to find good locations for incinerators for disposing PCBs. In Japan, it has been reported that about 5,500 tons of PCBs were incinerated in 1988–1989 by Kaneka Corp., and this is only one report on the disposal of PCBs. It is the present situation in Japan that there is little prospect of the disposal of PCBs. Since 1993, the possessors of PCBs, which cannot be subjected to disposal, are obliged to take custody of PCBs by notification from the Ministry of International Trade and Industry.

Under the aforementioned circumstances, studies are now being made on a method for rendering PCBs harmless by using a technique other than the above-described one. Hitherto, there have been proposed a method in which PCBs are changed into biphenyl, for instance, by causing dechlorination reaction by the use of photochemical means, a method in which PCBs are decomposed by microorganisms such as Pseudomonas, and a method in which PCBs are chemically decomposed by utilizing supercritical water. When PCBs are treated by one of these methods, there is no fear that dioxin is generated.

For example, in a method in which PCBs are decomposed by utilizing dechlorination reaction induced by ultraviolet-light irradiation, the progress of the dechlorination reaction has been generally confirmed by taking a reaction solution irradiated with ultraviolet light out of a reactor for carrying out dechlorination reaction, subjecting the reaction solution to such pretreatments as concentration and the removal of substances which will hinder the quantification of the PCBs, and quantifying the PCBs existing in the reaction solution by means of gas chromatography or the like.

However, in the above-described method for quantifying PCBs, it is necessary to take a reaction solution out of the reaction system, and also the pretreatments are complicated and require time, so that it has been difficult to continuously determine the progress of the decomposition reaction at real time.

To solve the aforementioned problems, there has been proposed, as described in Japanese Patent Laid-Open Publication No. 262171/1994, a unit which is provided to a device designed for decomposing halogenated organic compounds by using ultraviolet light, and which is used to measure the quantity of the decomposed residue of the organic compounds by obtaining the absorption spectrum of the reaction solution at real time. However, many of halogenated organic compounds have absorption bands in the ultraviolet region. It is therefore difficult to independently quantify, by using the absorption spectrum, the reaction products or intermediate products produced by complicated reactions, and the desired compound. Thus, there is yet room for improvement in this method.

Further, a video fluorescent monitor for determining the contour of spilt PCBs or PCB mineral oil is described in the specification of WO 93/13404. In this specification, it is described that a split of an insulating oil containing PCBs used for a transformer or condenser is observed by the fluorescent monitor. However, this fluorescent monitor is designed for observing the fluorescence of the mineral oil as a whole, and not for quantifying a specific compound, that is, PCBs contained in the mineral oil.

Japanese Patent Laid-Open Publication No. 304407/1994 describes a device for rendering injurious chlorine compounds harmless. In this publication, it is described that the undecomposed residue of PCBs is detected by an apparatus for monitoring the decomposition of PCBs. However, any specific method for measuring the quantity of the PCBs is not found in this publication.

SUMMARY OF THE INVENTION

A system for treating PCBs to render them harmless according to the present invention comprises:

(1) a device for carrying out the decomposition reaction of PCBs contained in a liquid having a known PCB concentration, and (2) a device for determining the quantity of the PCBs existing in the PCB-containing liquid taken out of the above device based on the value of the intensity of the light at a wavelength between 450 nm and 600 nm, both inclusive, which is emitted upon irradiation of the PCB-containing liquid with exciting light having a wavelength of 400 nm to shorter than 450 nm, that can excite the PCBs.

Another system for treating PCBs to render them harmless according to the present invention comprises:

(1) a device for carrying out the decomposition reaction of PCBs contained in a liquid having a known PCB concentration, and (2) a device for determining the quantity of the PCBs existing in the PCB-containing liquid taken out of the above device based on the value of the intensity of the light at a wavelength between 450 nm and 600 nm, both inclusive, which is emitted upon irradiation of the PCB-containing liquid with exciting light having a wavelength of 300 nm to shorter than 400 nm, that can excite the decomposition products of the PCBs.

A further system for treating PCBs to render them harmless according to the present invention comprises:

(1) a device for carrying out the decomposition reaction of PCBs contained in a liquid having a known PCB concentration, and (2) a device for determining the quantity of the PCBs existing in the PCB-containing liquid taken out of the above device based on the ratio between the value of the intensity of the light at a wavelength between 450 nm and 600 nm, both inclusive, which is emitted upon irradiation of the PCB-containing liquid with exciting light having a wavelength of 400 nm to shorter than 450 nm, that can excite the PCBs, and the value of the intensity of the light at a wavelength between 450 nm and 600 nm, both inclusive, which is emitted upon irradiation of the PCB=containing liquid with exciting light having a wavelength of 300 nm to shorter than 400 nm, that can excite the decomposition products of the PCBs.

A device for quantifying PCBs according to the present invention comprises a method for determining the quantity of PCBs existing in a PCB-containing liquid based on the value of the intensity of the light at a wavelength between 450 nm and 600 nm, both inclusive, which is emitted upon irradiation of the PCB-containing liquid with exciting light having a wavelength of 400 nm to shorter than 450 nm, that can excite the PCBs.

Another device for quantifying PCBs according to the present invention comprises a method for determining the quantity of PCBs existing in a PCB-containing liquid based on the value of the intensity of the light at a wavelength between 450 nm and 600 nm, both inclusive, which is emitted upon irradiation of the PCB-containing liquid with exciting light having a wavelength of 300 nm to shorter than 400 nm, that can excite the decomposition product of the PCBs.

A further device for quantifying PCBs according to the present invention comprises a method for determining the quantity of PCBs existing in a PCB-containing liquid based on the ratio between the value of the intensity of the light at a wavelength between 450 nm and 600 nm, both inclusive, which is emitted upon irradiation of the PCB-containing liquid with exciting light having a wavelength of 400 nm to shorter than 450 nm, that can excite the PCBs, and the value of the intensity of the light at a wavelength between 450 nm and 600 nm, both inclusive, which is emitted upon irradiation of the PCB-containing liquid with exciting light having a wavelength of 300 nm to shorter than 400 nm, that can excite the decomposition products of the PCBs.

A method for determining the progress of the decomposition reaction of PCBs according to the present invention comprises irradiating a PCB-containing liquid with exciting light having a wavelength of from 400 nm to shorter than 450 nm, that can excite the PCBs, measuring the intensity of the emitted light at a wavelength between 450 nm and 600 nm, both inclusive, and determining, based on the measured value, the quantity of the PCBs existing in the liquid during the decomposition process of the PCBs.

Another method for determining the progress of the decomposition reaction of PCBs according to the present invention comprises irradiating a PCB-containing liquid with exciting light having a wavelength of from 300 nm to shorter than 400 nm, that can excite the decomposition products of the PCBs, measuring the intensity of the emitted light at a wavelength between 450 nm and 600 nm, both inclusive, and determining, based on the measured value, the quantity of the decomposition products of the PCBs existing in the liquid during the decomposition process of the PCBs.

A further method for determining the progress of the decomposition reaction of PCBs according to the present invention comprises irradiating a PCB-containing liquid with exciting light having a wavelength of from 400 nm to shorter than 450 nm, that can excite the PCBs, measuring the intensity of the emitted light at a wavelength between 450 nm and 600 nm, both inclusive, irradiating the PCB-containing liquid with exciting light having a wavelength of from 300 nm to shorter than 400 nm, that can excite the decomposition products of the PCBs, measuring the intensity of the emitted light at a wavelength between 450 nm and 600 nm, both inclusive, and determining, based on the ratio between the two measured values, the quantity of the PCBs existing in the liquid during the decomposition process of the PCBS.

The present invention is based on such a finding that it is possible to distinguish PCBs from the decomposition products thereof by using an excitation spectrum (the details thereof will be described later), this finding being believed to be conventionally unknown.

According to the present invention, which has been accomplished on the basis of the above finding, the difficulty of determining the progress of the decomposition reaction of PCBs carried out in a conventional device for decomposing PCBs can be cleared, and a system for treating PCBs to render them harmless, capable of continuously determining the progress of the decomposition reaction of PCBs at real time by using a predetermined amount of a reaction solution taken out while the decomposition reaction of the PCBs is proceeding can be provided.

BRIEF DESCRIPTION OF THE DRAWINGS

In the drawings,

FIG. 1 is a graph showing a series of excitation spectra obtainable by irradiating a PCB-containing liquid with ultraviolet light (wavelength at observation: 480 nm);

FIG. 2 is a diagrammatical view of a system for treating PCBs to render them harmless according to the present invention;

FIG. 3 is a graph showing the relationship between the energy of ultraviolet light irradiated and the excitation spectral band intensity, or the ratio between the two excitation spectral band intensities, which energy and spectral band intensities were measured in Example 1;

FIG. 4 is a chart showing a part of the system for treating PCBs to render them harmless, in which the PCB content is measured.

DETAILED DESCRIPTION OF THE INVENTION

<Excitation Spectral Method/Principle of Measurement>

Figure 5:
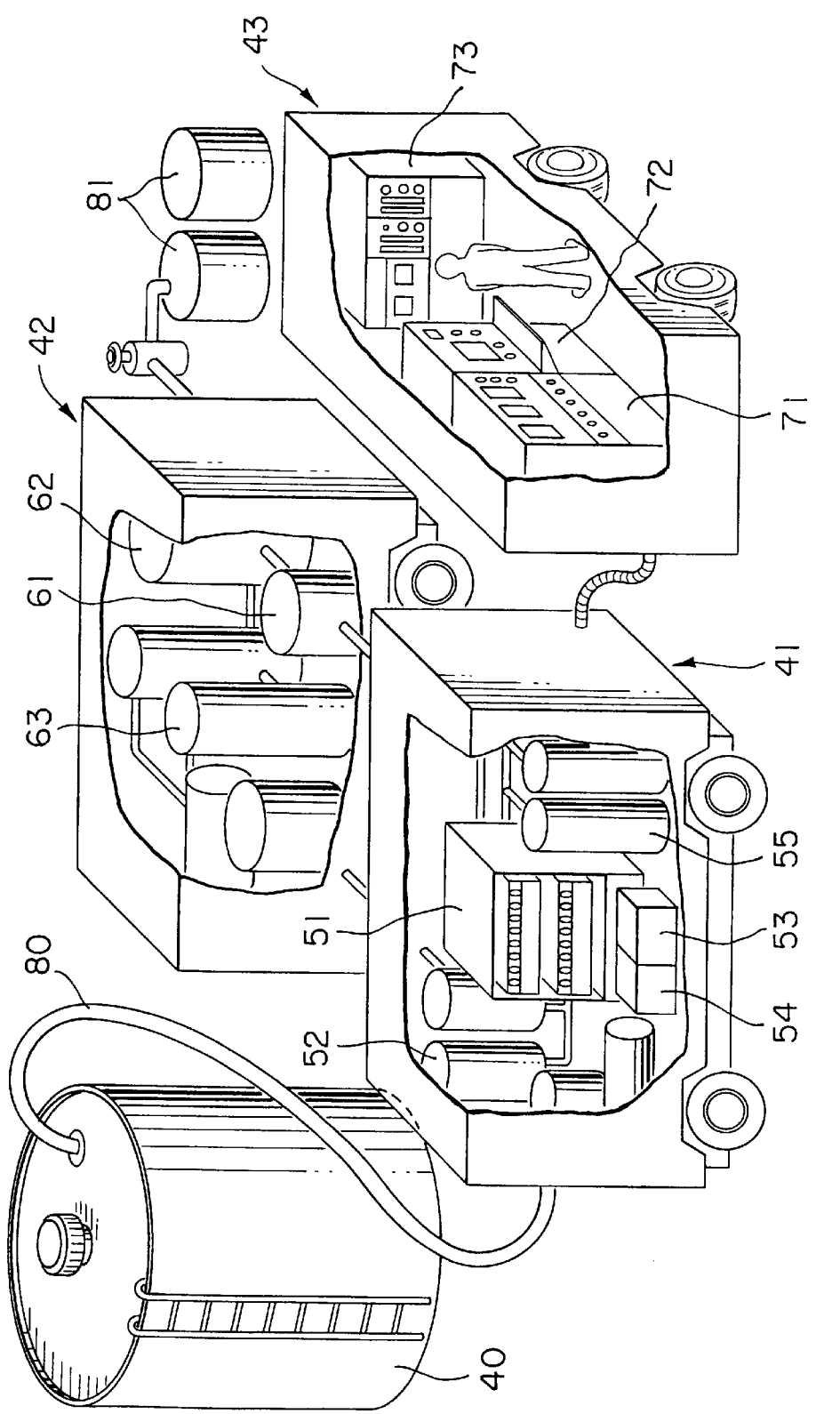
FIG. 5 is a diagrammatical view of a specific embodiment of the system for treating PCBs to render them harmless according to the present invention.

The system for treating PCBs to render them harmless according to the present invention employs an excitation spectral method which comprises irradiating an objective to be quantified with light having a specific wavelength to selectively excite the energy (wavelength) of the electron of the objective, and measuring the intensity of the light thus emitted by the objective to determine the quantity of the objective.

When it is tried to determine the progress of the decomposition of PCBs in a method in which chlorine groups are photochemically, chemically or microbiologically removed from the PCBs to decompose them into biphenyl, it is not desirable to take a reaction solution out of the decomposition reaction system when safety and production cost are taken into consideration. As one of the techniques capable of most effectively solving this problem, an optical technique of measurement can be considered.

The optical techniques include absorption spectral, emission spectral, excitation spectral, light scattering and infrared absorption methods. To quantify the remaining PCBs in a solution while the decomposition reaction of PCBs is proceeding, it is difficult to employ a light scattering method because sufficiently high sensitivity cannot be obtained; and it is also difficult to employ an infrared absorption method or absorption spectral method because the PCB concentration in the solution, and the distance of light transmitted through a sample are restricted. Further, by an absorption or emission spectral method, it is difficult to detect various PCBs having chlorine atoms in different numbers, biphenyl and decomposition products of PCBs because their absorption bands overlap the absorption bands of various organic molecules of solvents and the like.

It has now been found that PCBs can be quantified distinctively from the decomposition products thereof by an excitation spectral method in which PCBs are excited with light having a specific wavelength and the intensity of the emitted light is measured at a specific wavelength.

As an example, a case where the photolysis of a solution of PCBs and trichlorobenzene (hereinafter abbreviated to "3MCB") in isopropyl alcohol (hereinafter abbreviated to "IPA") is induced by irradiating the solution with ultraviolet light is shown below. The excitation spectra obtained by changing the wavelength of exciting light between 300 nm and 470 nm are as shown in FIG. 1, provided that the wavelength at which the intensity of the emitted light is measured is fixed at 480 nm. When the solution is irradiated with ultraviolet light, the excitation spectral band intensity between 310 nm and 380 nm is increased with time, whereas the excitation spectral band intensity between 390 nm and 460 nm is decreased with time. The PCBs contained in samples taken at various points of time are quantified on a GC-MS gas chromatography spectrum obtained. As a result, it was found that the peak of the excitation spectrum in the vicinity of 340 nm is attributed to the products produced by the dechlorination of PCBs and that the peak of the excitation spectrum in the vicinity of 425 nm is attributed to PCBs.

As far as we know, it has not been reported until now that PCBs can be distinguished from the decomposition products thereof by using an excitation spectroscopy. This is believed to be a new finding.

An excitation spectrum can be obtained by irradiating a fluorescent or phosphorescent substance with exciting light at the various wavelength thereof, and measuring the intensity of the emitted light at a specific wavelength; and it can be said that an excitation spectrum shows the dependency of excitation energy on emission energy. Namely, an excitation spectrum can also be considered to be a kind of absorption spectrum. However, the excitation spectral method is superior to the absorption spectral method in that only those species which emit light only when light having a specific wavelength is applied thereto can be quantified and that the concentration of the species and the distance of light transmitted through a sample are not restricted.

An excitation spectrum can be obtained by a known method. In the case of a dilute solution, a cell containing a sample is irradiated with exciting light, and the intensity of the light emitted by the sample upon the irradiation is measured at a right angle to the direction of the irradiation. On the other hand, when a solution has a high concentration, there is such a possibility that the light emitted by the solution when exciting light is applied thereto is absorbed by the solution (or solute) (this phenomenon is referred to as "reabsorption"), so that the light emitted is measured to have a decreased intensity. In this case, the effect of the reabsorption can be reduced by irradiating a cell containing a sample with exciting light, and measuring the emitted light at a point near the irradiation point on the surface of the cell. An excitation spectrum can also be obtained by other method suitably selected from known methods depending upon the conditions of a solution to be used.

In the case where PCBs are decomposed by means of dechlorination reaction, the reaction solution is to contain both PCBs and reaction products (most of the PCBs are considered to be converted into biphenyl). As mentioned previously, the quantity of PCBs contained in this reaction solution can be determined by irradiating the reaction solution with exciting light having a wavelength of from 400 nm to shorter than 450 nm, and measuring the intensity of the emitted light at a wavelength between 450 nm and 600 nm, both inclusive. On the other hand, the reaction products can be quantified by irradiating the reaction solution with exciting light having a wavelength of from 300 nm to shorter than 400 nm, and measuring the intensity of the emitted light at a wavelength between 450 nm and 600 nm, both inclusive. In the dechlorination reaction of PCBs, if either PCBs themselves or the reaction products thereof can be quantified, the quantity of the existing PCBs can be determined. Further, in the excitation spectral method, the measurement system is influenced by a change in sensitivity. In order to make this influence minimum to determine the quantity of the existing PCBs more precisely, the following manner can be employed: the intensity of the light emitted when exciting light having a wavelength of from 400 nm to shorter than 450 nm is applied, and that of the light emitted when exciting light having a wavelength of from 300 nm to shorter than 400 nm is applied are respectively measured at a wavelength between 450 nm and 600 nm, both inclusive, and the quantity of the existing PCBs is determined based on the ratio between the two intensities measured. The exciting light which is applied to excite PCBs is preferably light having a wavelength of from 415 nm to shorter than 435 nm, and the exciting light which is applied to excite the decomposition products of PCBs is preferably light having a wavelength of from 330 nm to shorter than 350 nm. In addition, the wavelength at which the intensity of the light emitted by the PCBs or decomposition products thereof is measured is preferably between 470 nm and 490 nm, both inclusive.

The measured value of the intensity of the emitted light is proportional to the quantity of the objective light-emitting compound (that is, PCBs or the dechlorinated products thereof, especially biphenyl). If it is necessary to know the absolute quantity of the objective compound, it can be obtained from a calibration curve of the intensity of the emitted light vs. the content of the objective compound, obtained by a preliminary test. Collation of the measured value with the calibration curve can also be made by a computer. In this case, the decomposition of PCBs can be monitored at real time.

<Device for Decomposing Polychlorobiphenyls>

The decomposition reaction of PCBs, the progress thereof being monitored in accordance with the above-described principle, can be carried out by any means as long as it is fit for the purpose. Moreover, PCB materials of any type can be subjected to the decomposition reaction.

Namely, to decompose PCBs, any reaction can be used in the system for treating PCBs to render them harmless according to the present invention. Specifically, a photochemical, microbiological or chemical method, or the like can be mentioned as a method for decomposing PCBs.

In the case where a photochemical method is employed, a solution or dispersion in which PCBs have been dissolved or dispersed is irradiated with light to induce photoreaction. The PCBs can thus be converted into biphenyl. The light to be used in this method is preferably one having high energy, and ultraviolet light is generally used. Specific examples of the light source include xenon lamps, mercury vapor lamps, and the like. Further, it is also possible to improve the conversion efficiency by the use of a catalyst such as titanium oxide in the reaction system.

The photoreaction caused in this method has not been made clear so far. However, in a system in which PCBs and isopropyl alcohol are co-existing, it is presumed that the photoreaction proceeds in accordance with the following scheme:

utilizing this property, PCBs can be decomposed microbiologically by the system of the present invention. Further, the above-described decomposition reaction utilizing photoreaction and the decomposition reaction induced by microorganisms can also be used in combination.

Furthermore, a device utilizing supercritical water may also be used as the device for decomposing PCBs contained

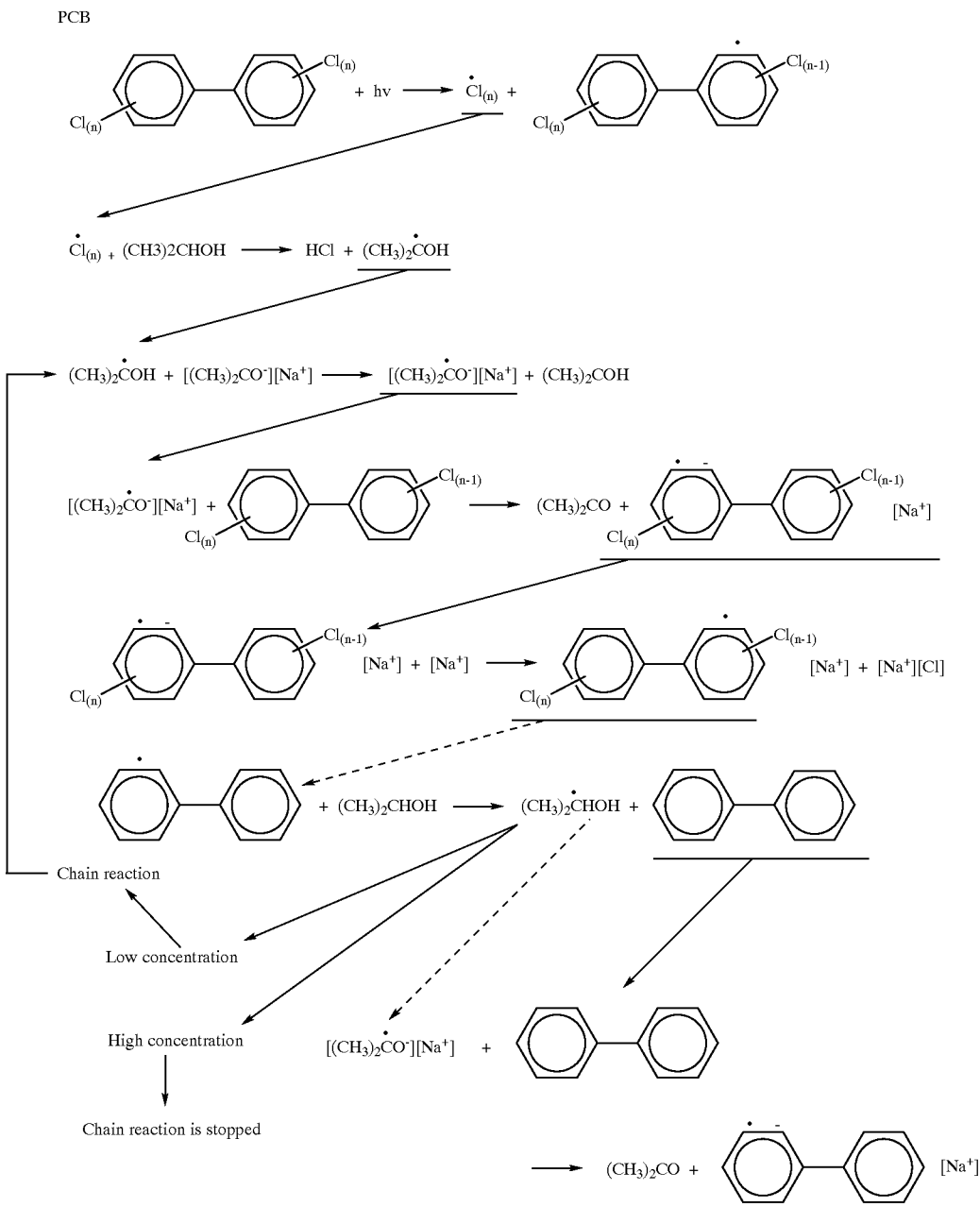

Namely, chlorine atoms contained in PCBs are eliminated one after another by isopropyl alcohol radical, and the PCBs are finally converted into biphenyl.

Further, it has also been known that PCBs are decomposed by some microorganisms belonging to the genus Pseudomonas, the genus Rhodococcus, or the like. By in the systems of the present invention. Supercritical water can be obtained by pressurizing water to 220 atmospheres or higher, and is compatible even with organic materials which are insoluble in water in an ordinary state. By utilizing this characteristic, it is possible to decompose PCBs. Namely, PCBs can be decomposed by a process in which PCBs are dissolved in supercritical water, and adding an oxidizing agent such as hydrogen peroxide is added to the solution.

The device for decomposing PCBs contained in the system for treating PCBs to render them harmless according to the present invention may employ any of the above-described methods. However, a device employing a photo-chemical method is preferred, and one employing a method in which PCBs are decomposed by ultraviolet-light irradiation is particularly preferred.

Various PCB materials which are different in their histories in use can be treated by this device for decomposing PCBs. However, PCB materials are often used as insulating oils or heat transfer media, so that typical PCB materials are liquids containing PCBs at relatively high levels.

Liquids containing PCBs at various levels can be treated by this device of the invention, and the suitable PCB concentration varies depending upon the actual means adopted for decomposing PCBs. However, if the means used for decomposing PCBs is a photochemical one, the PCB concentration in the reaction solution is, in general, 10% by weight or less, preferably from 1 to 5% by weight. Such a low level of the PCB concentration is also preferable when the excitation spectral method of the present invention is effected.

<Device for Quantifying PCBs>

The system for treating PCBs to render them harmless according to the present invention contains a device for quantifying PCBs, by which the concentration of PCBs is determined based on the excitation spectral band intensity measured at a specific wavelength in accordance with the previously-mentioned excitation spectral method. By this device, the quantity of the existing PCBs, that is, the progress of the decomposition reaction of PCBs can be determined at real time without requiring any special pretreatment, and the treatment for rendering PCBs harmless can thus be fully and sufficiently carried out.

Any device can be used for quantifying PCBs as long as it is fit for the purpose. However, the device for quantifying PCBs is basically composed of a unit for sampling a reaction solution, a unit for measuring the intensities of the exciting light to be applied for irradiation and of the light emitted upon the irradiation, and an analyzer of the measured values.

While the unit for sampling a reaction solution can be one by which a reaction solution is sampled batch-wise from the reaction system for carrying out the decomposition reaction of PCBs, it is preferable, in order to make a real-time measurement, that the reaction solution be fed from the unit for sampling to the unit for measurement through a pipe or the like.

Any apparatus can be used as a unit for measuring the intensities of the exciting light to be applied and of the light emitted. However, it is convenient to use an ordinary spectrofluorophotometer. In the case where the data obtained by the measurement are analyzed by transferring them to a computer or the like, it is preferable that this unit be equipped with an interface for transferring the out-put data to the computer.

As the analyzer of the measured values, the simplest one is a chart recorder or plotter. However, the detection of PCBs in extremely small amounts is required, so that the analyzer is preferably a digital analyzer using a computer. Further, it is preferable to control the driving of wavelength and the slit width in the above-described spectroscopes for exciting light and for fluorescence, and some others in the unit for measurement on the basis of the data obtained by this digital analyzer.

EXAMPLES

Example 1

Under irradiation of 10 cm$^3$ of an IPA solution containing PCBs having a chlorine group concentration of 40,000 ppm and 3MCB having a chlorine group concentration of 80,000 ppm with ultraviolet light by using a low-pressure mercury vapor lamp, samples were taken sequentially, and used to obtain the excitation spectrum of the IPA solution. The excitation spectrum was expressed numerically by measuring the excitation spectral band intensities by applying exciting light of 425 nm and exciting light of 337 nm, and calculating the ratio between the two intensities measured. At the same time, the samples taken at various points of time were respectively subjected to gas chromatography to measure the concentration of the chlorine group remaining in the solution at each point of time. The excitation spectrum and the concentration of the remaining chlorine group were thus calibrated. By applying this calibration to the following device for decomposing PCBs, a device for carrying out the photolysis of PCBs was assembled.

A diagrammatical view of the device for decomposing PCBs is shown in FIG. 2. This device is composed of a reaction vessel 1 in which an IPA solution of PCBs is placed and the decomposition reaction of the PCBs is carried out, a low-pressure mercury vapor lamp 2 which is a radiation source of ultraviolet light to be applied to decompose the PCBs, a spectrofluorophotometer 3 which is used to obtain the excitation spectrum of the solution, a personal computer 4 for calculating the concentration of the existing PCBs from the excitation spectrum obtained by the spectrophotometer, and a pipe 5 with which a sample solution is fed to the spectrophotometer.

In the reaction vessel 1 of this device was placed 10 cm$^3$ of an IPA solution containing PCBs having a chlorine group concentration of 40,000 ppm and 3 MCB having a chlorine group concentration of 80,000 ppm. This solution was irradiated with ultraviolet light by the use of the low-pressure mercury vapor lamp 2, thereby carrying out the photolysis of the PCBs. During the photolysis, the personal computer 4 showed that the concentration of the remaining chlorine group was gradually decreased (FIG. 3). In order to confirm this, samples were taken sequentially, and the concentration of the PCBs contained in each sample was determined on a GC-MS gas chromatography mass spectrum obtained. As a result, the change in the PCB concentration was found to agree with that in the concentration of the remaining chlorine group in FIG. 3.

It is noted that there was observed such a phenomenon that the concentration of the remaining chlorine group was temporally increased after the initiation of the ultraviolet-light irradiation. The cause of this phenomenon is not clear. However, the concentration of the remaining chlorine group estimated from the excitation spectrum agrees with the value obtained from the GC-MS gas chromatography mass spectrum. It is therefore believed that the concentration of the remaining chlorine group estimated from the excitation spectrum is correct.

Example 2

FIG. 4 shows, in great details, a fluorescent spectrophotometer 3 and a computer 4 which are provided to another device for decomposing PCBs according to the present invention.

Light radiated from a light source 11, for instance, a xenon lamp, passes through a lens 12, and is resolved by a spectroscope 13 for exciting light. This spectroscope 13 for exciting light is equipped with a stepping motor 14. The light separated by the spectroscope 13 is introduced, by a beam splitter 15, to an exciting light detector 16, and also to a sample cell 18 through a lens 17. To the sample cell 18, a sample solution is fed from the reaction system (not illustrated) by a pump 19 at real time. Organic compounds contained in the sample emit fluorescence when excited by the exciting light. This fluorescence is led to a spectroscope 22 by the aid of a mirror 20 and a lens 21, and resolved. The intensity of the fluorescence is measured by a fluorescence detector 24.

With respect to the intensity of the fluorescence measured, the data obtained from the fluorescence detector 24 may be directly recorded by a chart recorder 25. Alternatively, the PCB concentration may be calculated from the intensity of the fluorescence measured by the fluorescence detector 24 and the intensity of the exciting light measured by the exciting light detector 26 by transferring the data on these intensities to a computer 30 through an A/D converter 26 and an I/O bus 29. The data on the PCB concentration calculated can be stored in an external memory such as a hard disk or a ram disk, or recorded by a plotter 28 through a D/A converter 27. Further, it is also possible to control the stepping motors respectively provided to the spectroscopes and the slit widths of the spectroscopes by using the computer 30.

Example 3

FIG. 5 is a diagrammatical view showing a specific embodiment of the system for treating PCBs to render them harmless according to the present invention. In FIG. 5, the device for decomposing PCBs of the present invention is divided into sections, and units belonging to each section are placed on a trailer. A trailer 41 is for a section covering the photolysis of PCBs, and on this trailer are placed a mixing/stirring tank 51 in which a reaction solution is prepared prior to the decomposition reaction of PCBS, a light source/photoreaction vessel 52 containing a light source for inducing photolysis and a reaction vessel in which the reaction solution is allowed to react, a unit 53 for monitoring the decomposition of PCBs, a unit 54 for measuring the concentration of PCBs with high accuracy, and a buffer tank 55.

A trailer 42 is for a section covering the post-treatment of the reaction solution which has been rendered harmless by the decomposition reaction of PCBs, and on this trailer are placed a preheater 61, an evaporator 62 and a still 63.

A trailer 43 is for a section covering the monitoring and control of each treatment, and on this trailer are placed a controller 71 for the current source of the light source, a controller 72 for the centralized monitor, and a preliminary analyzer 73.

Since PCBs are generally stored in a storage tank 40, those devices which are needed to render PCBs harmless are carried to a site close to the storage tank. At this site, the PCBs can be fed, by the use of a tube 80, to the system for treating PCBs to render them harmless, and the product which has been made harmless by the treatment can be recovered in a recovery tank 81. Thus, by placing, on trailers, the system for treating PCBs to render them harmless according to the present invention, it becomes possible to treat PCBs stored in a storage tank to render them harmless without building a facility for the purpose.

We claim:

1. A system for treating polychlorobiphenyls to render them harmless, comprising:

(1) a device for carrying out the decomposition reaction of polychlorobiphenyls contained in a liquid having a known polychlorobiphenyl concentration, and (2) a device for determining the quantity of the polychlorobiphenyls existing in the polychlorobiphenyl-containing liquid taken out of the device for carrying out the decomposition reaction of polychlorobiphenyls by the value which is obtained by irradiating the polychlorobiphenyl-containing liquid with exciting light having a wavelength of 400 nm or longer and shorter than 450 nm, that can excite the polychlorobiphenyls, and measuring the intensity of the emitted light at a wavelength between 450 nm and 600 nm.

2. The system for treating polychlorobiphenyls to render them harmless according to claim 1, wherein the device for carrying out the decomposition reaction of polychlorobiphenyls utilizes a photochemical reaction.

3. The system for treating polychlorobiphenyls to render them harmless according to claim 2, wherein the photochemical reaction is induced by ultraviolet-light irradiation.

4. The system for treating polychliorobiphenyls to render them harmless according to claim 1, wherein the device for carrying out the decomposition reaction of polychlorobiphenyls and the device for determining the quantity of the polychlorobiphenyls are connected with a pipe for feeding the polychlorobiphenyl-containing liquid to the device for determining the quantity of the polychlorobiphenyls.

5. A system for treating polychlorobiphenyls to render them harmless, comprising:

(1) a device for carrying out the decomposition reaction of polychlorobiphenyls contained in a liquid having a known polychlorobiphenyl concentration, and (2) a device for determining the quantity of the polychlorobiphenyls existing in the polychlorobiphenyl-containing liquid taken out of the device for carrying out the decomposition reaction of polychlorobiphenyls by the value which is obtained by irradiating the polychlorobiphenyl-containing liquid with exciting light having a wavelength of 300 nm or longer and shorter than 400 nm, that can excite the decomposition products of the polychlorobiphenyls, and measuring the intensity of the emitted light at a wavelength between 450 nm and 600 nm.

6. The system for treating polychlorobiphenyls to render them harmless according to claim 5, wherein the device for carrying out the decomposition reaction of polychlorobiphenyls utilizes a photochemical reaction.

7. The system for treating polychlorobiphenyls to render them harmless according to claim 6, wherein the photochemical reaction is induced by ultraviolet-light irradiation.

8. The system for treating polychlorobiphenyls to render them harmless according to claim 5, wherein the device for carrying out the decomposition reaction of polychlorobiphenyls and the device for determining the quantity of the polychlorobiphenyls are connected with a pipe for feeding the polychlorobiphenyl-containing liquid to the device for determining the quantity of the polychlorobiphenyls.

9. A system for treating polychlorobiphenyls to render them harmless, comprising:

(1) a device for carrying out the decomposition reaction of polychlorobiphenyls contained in a liquid having a known polychlorobiphenyl concentration, and (2) a device for determining the quantity of the polychlorobiphenyls existing in the polychlorobiphenyl-containing liquid taken out of the device for carrying out the decomposition reaction of polychlorobiphenyls by the ratio between the value which is obtained by irradiating the polychlorobiphenyl-containing liquid with exciting light having a wavelength of 400 nm or longer and shorter than 450 nm, that can excite the polychlorobiphenyls, and measuring the intensity of the emitted light at a wavelength between 440 nm and 600 nm, and the value which is obtained by irradiating the polychlorobiphenyl containing liquid with exciting light having a wavelength of 300 nm or longer and shorter than 400 nm, that can excite the decomposition products of the polychloro-biphenyls, and measuring the intensity of the emitted light at a wavelength between 450 nm and 600 nm.

10. The system for treating polychlorobiphenyls to render them harmless according to claim 9, wherein the device for carrying out the decomposition reaction of polychlorobiphenyls utilizes a photochemical reaction.

11. The system for treating polychlorobiphenyls to render them harmless according to claim 10, wherein the photochemical reaction is induced by ultraviolet-light irradiation.

12. The system for treating polychlorobiphenyls to render them harmless according to claim 9, wherein the device for carrying Out the decomposition reaction of polychlorobiphenyls and the device for determining the quantity of polychlorobiphenyls are connected with a pipe for feeding the polychlorobiphenyl-containing liquid to the device for determining the quantity of the polychlorobiphenyls.

13. A device for quantifying polychlorobiphenyls, in which the quantity of polychlorobiphenyls contained in a polychlorobiphenyl-containing liquid is determined by the value which is obtained by irradiating the polychlorobiphenyl-containing liquid with exciting light having a wavelength of 400 nm or longer and shorter than 450 nm, that can excite the polychlorobiphenyls, and measuring the intensity of the emitted light at a wavelength between 450 nm and 600 nm.

14. A device for quantifying polychlorobiphenyls, in which the quantity of polychlorobiphenyls contained in a polychlorobiphenyl-containing liquid is determined by the value which is obtained by irradiating the polychlorobiphenyl-containing liquid with exciting light having a wavelength of 300 nm or longer and shorter than 400 nm, that can excite the decomposition products of the polychlorobiphenyls, and measuring the intensity of the emitted light at a wavelength between 450 nm and 600 nm.

15. A device for quantifying polychlorobiphenyls, in which the quantity of polychlorobiphenyls contained in a polychlorobiphenyl-containing liquid is determined by the ratio between the value which is obtained by irradiating the polychlorobiphenyl-containing liquid with exciting light having a wavelength of 400 nm or longer and shorter than 450 nm, that can excite the polychlorobiphenyls, and measuring the intensity of the emitted light at a wavelength between 450 nm and 600 nm, and the value which is obtained by irradiating the polychlorobiphenyl-containing liquid with exciting light having a wavelength of 300 nm or longer and shorter than 400 nm, that can excite the decomposition products of the polychlorobiphenyls, and measuring the intensity of the emitted light at a wavelength between 450 nm and 600 nm.

* * * * *

UNITED STATES PATENT AND TRADEMARK OFFICE
CERTIFICATE OF CORRECTION

PATENT NO. : 5,937,267
DATED : August 10, 1999
INVENTOR(S) : Kenji TODORI, et al.

It is certified that error appears in the above-identified patent and that said Letters Patent is hereby corrected as shown below:

On the title page, item [73], the assignee's name should be:

--Kabushiki Kaisha Toshiba--

Signed and Sealed this

Sixteenth Day of May, 2000

Attest:

Q. TODD DICKINSON

*Attesting Officer*   *Director of Patents and Trademarks*